US010988371B2

(12) United States Patent
Logsdon

(10) Patent No.: US 10,988,371 B2
(45) Date of Patent: Apr. 27, 2021

(54) METHODS OF MANUFACTURING MEDICAL PADS

(71) Applicant: Stephen Nicholas Logsdon, St. Louis, MO (US)

(72) Inventor: Stephen Nicholas Logsdon, St. Louis, MO (US)

( * ) Notice: Subject to any disclaimer, the term of this patent is extended or adjusted under 35 U.S.C. 154(b) by 296 days.

(21) Appl. No.: 15/976,521

(22) Filed: May 10, 2018

(65) Prior Publication Data
US 2018/0362328 A1  Dec. 20, 2018

Related U.S. Application Data

(60) Provisional application No. 62/504,315, filed on May 10, 2017.

(51) Int. Cl.
| *B68G 3/02* | (2006.01) |
| *A47C 27/14* | (2006.01) |
| *B68G 7/05* | (2006.01) |
| *A47C 31/00* | (2006.01) |
| *B08B 7/00* | (2006.01) |
| *A61G 13/12* | (2006.01) |
| *A47C 27/08* | (2006.01) |
| *A61G 7/057* | (2006.01) |
| *A61G 7/075* | (2006.01) |
| *B68G 15/00* | (2006.01) |
| *A61B 46/10* | (2016.01) |
| *A61B 46/20* | (2016.01) |
| *A61B 50/15* | (2016.01) |
| *A61G 5/10* | (2006.01) |
| *A61G 5/12* | (2006.01) |
| *A61B 17/00* | (2006.01) |

(52) U.S. Cl.
CPC .............. *B68G 3/02* (2013.01); *A47C 27/085* (2013.01); *A47C 27/14* (2013.01); *A47C 31/007* (2013.01); *A61B 46/10* (2016.02); *A61B 46/20* (2016.02); *A61B 50/15* (2016.02); *A61G 5/10* (2013.01); *A61G 7/05738* (2013.01); *A61G 7/075* (2013.01); *A61G 13/127* (2013.01); *B08B 7/0057* (2013.01); *B68G 7/05* (2013.01); *B68G 15/00* (2013.01); *A61B 2017/00526* (2013.01); *A61G 5/1043* (2013.01); *A61G 5/125* (2016.11); *A61G 5/127* (2016.11); *A61G 7/0755* (2013.01); *A61G 13/1235* (2013.01); *A61G 13/1245* (2013.01)

(58) Field of Classification Search
CPC .. B68G 3/02; A61L 2/10; A61B 46/10; A61B 46/20; A61B 50/15; A47C 27/085; A47C 27/14

See application file for complete search history.

(56) References Cited

U.S. PATENT DOCUMENTS

| 5,697,946 | A | 12/1997 | Hopper et al. |
| 5,873,869 | A * | 2/1999 | Hammons ............... A61L 15/24 |
| | | | 604/385.01 |
| 6,524,283 | B1 | 2/2003 | Hopper et al. |
| 7,235,064 | B2 | 6/2007 | Hopper et al. |
| 8,186,587 | B2 | 5/2012 | Zmood et al. |
| 8,282,665 | B2 | 10/2012 | Kieturakis et al. |
| 8,558,699 | B2 | 10/2013 | Butler et al. |
| 9,262,659 | B2 | 2/2016 | Baker et al. |
| 2015/0342635 | A1 | 12/2015 | Tsamir et al. |

OTHER PUBLICATIONS

Derwent Abstrct of KR 2011049432 A, published: Nov. 2009, inventor: Geon (Year: 2009).*
Nacul et al., Effectiveness of a reusable low-cost balloon trocar dissection device in the creation of peritoneal space during endoscopic surgery. An experimental study in swine., Acta Cirurgica Brasileira, 2015, vol. 30, No. 9, pp. 646-653.
www.medicalexpo.com/prod/aesculap/product-70641-659776. html, Product description of Laparoscopic trocar Herloon System, 2 pages.

* cited by examiner

*Primary Examiner* — Sean E Conley
(74) *Attorney, Agent, or Firm* — Polsinelli PC

(57) ABSTRACT

The present disclosure relates to medical pads and methods of manufacturing medical pads.

12 Claims, No Drawings

METHODS OF MANUFACTURING MEDICAL PADS

CROSS REFERENCE TO RELATED APPLICATIONS

This application claims the benefit of U.S. provisional patent application No. 62/504,315, filed May 10, 2017, the disclosure of which is herein incorporated by reference in its entirety.

FIELD OF THE INVENTION

The present disclosure relates to medical pads, and materials and methods for manufacturing them.

SUMMARY OF THE INVENTION

In one aspect, the present disclosure provides a method for manufacturing a medical pad from a compromised medical pad, wherein the compromised medical pad comprises a fill material and an external cover surrounding the fill material, the method comprising: extracting the fill material from the external cover of the compromised medical pad; exposing the extracted fill material to UV-C output from a UV-C source for a time and under conditions sufficient to achieve at least a 3 log reduction in surface level microorganism activity to produce decontaminated fill material; and covering the decontaminated fill material with a new external cover. The method may further comprise inspecting the fill material for gross contamination after extracting the fill material from the external cover; discarding the fill material if gross contamination is observed; and if gross contamination is not observed, proceeding to expose the extracted fill material to the UV-C output.

In another aspect, the present disclosure provides a method for preparing a medical pad for a second use following at least a first use, the method comprising: removing an external cover of the medical pad; inspecting the fill material for gross contamination after removing the external cover; discarding the fill material if gross contamination is observed; if gross contamination is not observed, exposing the fill material to a UV disinfection protocol sufficient to achieve at least a 3 log reduction in surface level activity of microorganism to produce decontaminated fill material; and covering the decontaminated fill material with a new external cover.

In any of the methods, the exposure of the fill material to UV-C output can be for example for a time and under conditions sufficient to achieve at least a 6 log reduction in surface level microorganism activity on the fill material. The fill material may comprise at least one material selected from polymer foam, air-filled polymer pockets and a polymer gel, or any combination thereof. The medical pad can be for example a surgical pad, a wheelchair pad, or gurney pad or a bed pad.

For example, in any of the methods the exposure to a UV-C source can comprise: suspending the fill material to expose a first surface of the fill material to the UV-C source; activating the UV-C source to produce the UV-C output; directing the UV-C output toward the first surface for a period of at least about 10 minutes; repositioning the fill material to expose at least a second surface of the fill material; directing the UV-C output toward the second surface for a period of at least about 10 minutes. Alternatively, in any of the methods, the exposure to a UV-C source can comprise: positioning the fill material on a support structure to expose a first surface of the material, wherein the support is covered with a disposable cover; activating the UV-C source to produce a UV-C output; directing the UV-C output toward the first surface for a period of at least about 10 minutes; inverting the fill material on the support to expose at least a second surface of the fill material; directing the UV-C output toward the second surface for a period of at least about 10 minutes. In any of the methods, the UV exposure can be sufficient to achieve at least 99.999999% reduction in surface level activity of microorganisms. The UV-C source can comprise for example an Evergreen EDU-435 device. In any of the methods, a new external cover can be comprised in whole or in part of Sure-Chek® cover material.

In another aspect, the present disclosure provides a medical pad prepared according to any of the methods described herein. The present disclosure encompasses a medical pad comprising decontaminated fill material extracted from a used medical pad comprising the fill material and an external cover enclosing the fill material. In any medical pad as described herein, a new external cover can be comprised in whole or in part of Sure-Chek® cover material.

DETAILED DESCRIPTION OF THE DISCLOSURE

The present disclosure provides new materials and methods for manufacturing medical pads.

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms as used herein and in the claims shall include pluralities and plural terms shall include the singular.

The use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are well known and commonly used in the art. The methods and techniques of the present disclosure are generally performed according to conventional methods well known in the art and as described in various general and more specific references that are cited and discussed throughout the present specification unless otherwise indicated. Any chemical, enzymatic or staining reactions, or purification techniques are performed according to manufacturer's specifications and protocols, as commonly accomplished in the art or as described herein. The nomenclatures used in connection with, and the laboratory procedures and techniques of, analytical chemistry, synthetic organic chemistry, and medicinal and pharmaceutical chemistry described herein are also well known and commonly used in the art. Standard techniques are used for chemical syntheses, chemical analyses, pharmaceutical preparation, formulation, delivery, diagnosis and treatment of all subjects, human and animal.

Unless otherwise indicated herein, methods and procedures are performed according to conventional methods well known in the art.

As used herein, the term "medical pads" refers to any pad used in a medical or patient care setting, including but not limited to surgical table pads, spine table pads, pads for any table used for a medical procedure, chair pads and wheelchair pads (including arm rest pads), knee scooter pads, bed pads, gurney pads, and the like. The present disclosure relates to any other pads used in a medical or patient care setting which include a moisture-resistant or moisture-proof external cover material enclosing a soft fill material.

Hospital Acquired Infections (HAI's) are now becoming the single largest issue to health care providers nationally. Under the reimbursement structure of the Affordable Care Act (ACA), every health care facility is compelled to perform "Root Cause Analysis" to determine the exact source of HAI infections, because reimbursement is denied for expenses associated with HAI-caused hospital stays. Millions of dollars are being spent to reduce and eliminate HAIs. The Joint Commission and The State Survey Agency, the top hospital credentialing organizations, have dramatically increased policing of the condition of pads used in operating rooms, stretchers and medical pads in general. Concerns about causing HAIs means that any pads with damage to the external cover are deemed to have compromised the internal soft fill material (typically a foam, air pocket, gel material or the like), even if they have never been used. In fact, when any holes or other defects in medical pad covers are found during inspections, the Joint Commission and State Survey Agency currently issues "write-ups" of all accredited facilities. Currently, compromised pads are simply disposed of, at great cost and waste.

The methods and medical pads described herein are based in part on the discovery that fill material of medical pads can be suitably decontaminated for re-use in new medical pads that pass the required re-inspections and thus can be used safely in a medical setting requiring sterile or highly decontaminated conditions and materials. UV disinfection has been used in hospitals to decontaminate smooth, typically non-porous room surfaces such as walls and floors by killing challenging organisms that can cause serious issues for patients in hospitals today. When properly delivered to surgical room surfaces, UV effectively kills many known pathogens including *C. Diff*, MRSA, *E. coli* and even Ebola virus.

The inventor has succeeded in discovering a new way to deliver UV technology to suitably decontaminate the soft material used as fill in medical pads (e.g., medical foam, air pocket, or gel materials). Starting with a used medical pad, or a medical pad with a compromised external cover, the method comprises removing the external cover and exposing the fill material within. Put another way, the fill material is extracted from the external cover. The external cover is discarded. The fill material is examined for evidence of gross contamination, such as stains from bodily fluids such as blood or urine. If gross contamination or evidence thereof is observed, the fill material is also discarded. If gross contamination is not observed, the extracted fill material is exposed to UV-C output from a UV-C source according to the protocol detailed further herein below, which provides conditions sufficient to achieve at least a 3 log reduction in surface level microorganism activity, to produce decontaminated fill material. The UV protocol described herein is sufficient to achieve a 6 log reduction in surface level microorganism activity, or a 99.999999% reduction in surface microorganism activity. The decontaminated fill material is then recovered with new cover material to produce a medical pad that passes the required accreditation inspections and thus can be used safely in a medical setting requiring sterile or highly decontaminated conditions and materials. Any cover material as described herein can be used. By way of non-limiting example, decontaminated fill material can be recovered with a new cover comprising Sure-Chek® cover technology on all or a portion, for example just the bottom, of the medical pad. Sure-Chek® cover material continues to disinfect after the recovering step.

Fill material of the medical pads is for example any conventional support material used in medical pads, such as but not limited to foams, gel materials, and air pocket materials. Foams include for example any polymer foam, such as polyester or polyether polyurethane foams (e.g., Serofoam®), tri-laminate foams, posturepedic type foams, and any other type of foam used in products used in a medical or patient care setting. Foam can be molded into various forms, including for example a segmented, waffled or egg crate form. Gel materials include, for example, polyvinyl alcohol gels, and can optionally be configured in a form having multiple gel bladders. Air pocket materials include, for example, a polymer such as a polyvinyl formed to create multiple air pockets or bladders. The fill material may comprise any combination of two or more fill materials, such as a combination of a gel and a foam, or a gel and an air pocket material. Fill material may comprise a multiple layer, e.g., a double, triple or quadruple layer of two or more different fill materials.

The cover material of the medical pads is any moisture resistant or moisture-proof textile suitable for use in healthcare facilities. Preferably the cover material has other features preferred for use in health care settings, such as stain resistance, flame resistance, and hypoallergenicity. Any cover material that itself acts as a disinfecting agent or can be used. Optionally, two different textiles can be used for the portion of external cover over the top surface and the portion of cover over the bottom surface of the medial pad. Non-limiting examples of cover material are Sure-Chek® textiles, commercially available from Herculite® of Emigsville, Pa. A Sure-Chek® textile can be used as the cover material for all or a portion of the new external cover. Sure-Chek® top surface fabrics include, for example, Sure-Chek Fusion® I HP, Sure-Chek Fusion III HP, Sure-Chek Comfort®, Sure-Chek Sure-thane®, Linea® 70, Sure-Chek 210d Nylon, Sure-Chek Soft®, Sure-Chek 6, Sure-Chek 20, Sure-Chek Clear Chek®, Sure-Chek 44, Sure-Chek XL®, Sure-Chek 44XL, Herculex®II, Sure-Chek 80, Sure-Chek PF, Sure-Chek SoftChek. Sure-Chek® bottom surface fabrics include Sure-Chek 20, Sure-Chek Clear Chek®, Sure-Chek 44, Sure-Chek XL®, Sure-Chek 44XL, Sure-Chek 80, Herculex®II.

After extracting the fill material and examining the fill material for evidence of gross contamination, suitably uncompromised fill material is subjected to UV decontamination. For exposure to the UV-C source, any means of holding, fixing, supporting or hanging can be used to maintain the fill material in substantially one position during exposure to the UV-C source. The fill material is typically substantially planar, and will have two main planar surfaces. Of these two surfaces, for example, a first or top surface is the surface on which a patient will rest. A second or bottom surface is the surface that will be in contact with a supporting structure such as a bed, surgical table, gurney, wheelchair, or the like. Although the fill material may assume any irregular or regular shape, most medical pads and the fill extracted from them are substantially quadrangular, e.g., substantially square, rectangular or trapezoidal, with a thickness ranging from less than an inch to several inches depending on the material and the purpose of the pad.

In one aspect, the method involves hanging the exposed fill material, for example using hooks, a hanging line or pole, hangers or the like, to expose the first surface directly to the UV-C source such that the UV-C output impinges substantially on the first surface. The UV-C source is positioned at a distance of about 2 feet to about 5 feet, preferably about 3 feet, from the exposed surface of the pad, and turned on for at least about 10 minutes. It will be understood that any distance from 2 feet to 5 feet inclusive can be used, including but not limited to 2.5 feet, 3 feet, 3.5 feet, 4 feet, and 4.5 feet. The fill material is then repositioned to expose the second surface directly to the UV-C source, and the UV exposure step repeated for the second surface, in which the UV-C source is turned on again for at least about 10 minutes.

Alternatively, uncompromised fill material extracted from a used or compromised cover can be laid out on a work surface such as a table or bench, with the top or bottom surface facing up. The UV-C source is positioned at a distance of about 2 feet to about 5 feet as explained above, to expose the first surface directly to the UV-C source such that the UV-C output impinges substantially on the first surface. The UV-C source is turned on for at least about 10 minutes. The fill material is then flipped over to expose the second surface directly to the UV-C source, and the UV exposure step repeated for the second surface, in which the UV-C source is turned on again for at least about 10 minutes. Optionally before the first UV exposure of the first surface, the work surface can be covered with a clean, disposable paper covering and the fill material positioned thereon. Following the UV exposure step with the first surface, when the fill material is being flipped to expose the second surface, the paper covering is discarded. Optionally the paper covering can be replaced with a second, clean paper covering. Once the second surface is suitably exposed to the UV-C source, the UV exposure step is repeated for the second surface, in which the UV-C source is turned on again for at least about 10 minutes.

The UV-C source preferably provides UV light at wavelengths between about 200 and about 300 nanometers, or substantially within the UV-C wavelength range. For example, a commercially available portable UV-C lamp used for decontaminations of hard room surfaces can be used. An exemplary but non-limiting UV-C source used for room decontaminations is the EDU-435 manufactured by Evergreen UV of Memphis, Tenn., which features four (4) 35 W Philips Germicidal UV Lamps (UV-C) for high output and maximum efficiency in a very small footprint (10" W×10" D×15" H). An alternative device is the Tru-D Smart UVC device commercially available from Tru-D SmartUVC of Memphis, Tenn. For example, a "mini" Tru-D Smart UVC can be used.

The following example is included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

EXAMPLE

Example 1

SSM St. Louis University Hospital

SSM St. Louis University Hospital (SLUH) in St. Louis, Mo. was written up by the state of Missouri Hospital Inspector for holes found in two of their Mizuho 10' spine table pads. Fill material from both of the compromised pads was extracted, inspected, decontaminated by exposure to UV-C output from an Evergreen EDU-435 device, according to the UV exposure protocol described herein above, and re-covered with a new external cover including a Sure-Chek® material on the bottom surface. The resulting two pads were subsequently re-examined by the State and were approved for use without issue.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

What is claimed is:

1. A method for manufacturing a medical pad from a compromised medical pad, wherein the compromised medical pad comprises a fill material and an external cover surrounding the fill material, the method comprising: extracting the fill material from the external cover of the compromised medical pad; and exposing the extracted fill material to UV-C output from a UV-C source for a time and under conditions sufficient to achieve at least a 3 log reduction in surface level microorganism activity to produce decontaminated fill material; and covering the decontaminated fill material with a new external cover.

2. The method of claim 1, further comprising inspecting the fill material for gross contamination after extracting the fill material from the external cover and discarding the fill material if gross contamination is observed, and if gross contamination is not observed, proceeding to expose the extracted fill material to the UV-C output.

3. The method of claim 1, wherein the exposure of the fill material to UV-C output is for a time and under conditions sufficient to achieve at least a 6 log reduction in surface level microorganism activity on the fill material.

4. The method of claim 1, wherein the fill material comprises at least one material selected from polymer foam, air-filled polymer pockets and a polymer gel.

5. The method of claim 1, wherein the fill material comprises at least one material selected from the group consisting of a polyester or polyether polyurethane foam, a tri-laminate foam, a posturepedic-type foam, a polyvinyl alcohol gel, and a polyvinyl forming air pockets.

6. The method of claim 1, wherein the medical pad is a surgical table pad, a spine table pad, a pad used on any table used for a medical procedure, a chair pad, a wheelchair pad, an arm rest pad, a knee scooter pad, a bed pad, or a gurney pad.

7. The method of claim 1, wherein the exposure to a UV-C source comprises:
suspending the fill material to expose a first surface of the fill material to the UV-C source;
activating the UV-C source to produce the UV-C output; directing the UV-C output toward the first surface for a period of at least about 10 minutes; repositioning the fill material to expose at least a second surface of the fill material; directing the UV-C output toward the second surface for a period of at least about 10 minutes.

8. The method of claim 1 wherein the exposure to a UV-C source comprises:

positioning the fill material on a support structure to expose a first surface of the material, wherein the support is covered with a disposable cover; activating the UV-C source to produce a UV-C output; directing the UV-C output toward the first surface for a period of at least about 10 minutes; inverting the fill material on the support to expose at least a second surface of the fill material; directing the UV-C output toward the second surface for a period of at least about 10 minutes.

9. The method of claim 6 or 7, wherein the UV exposure is sufficient to achieve at least 99.999999% reduction in surface level activity of microorganisms.

10. The method according to any of claims 1-8, wherein the UV-C source comprises an Evergreen EDU-435 device.

11. The method of claim 1, further comprising recovering the decontaminated fill material with a new external cover.

12. The method of claim 11, wherein the new external cover comprises an antimicrobial fabric.

\* \* \* \* \*